US00RE39102E

(19) United States
(12) Reissued Patent
Schulz et al.

(10) Patent Number: US RE39,102 E
(45) Date of Reissued Patent: May 23, 2006

(54) OPTICAL FIBER PROBE FOR POSITION MEASUREMENT

(75) Inventors: Waldean A. Schulz, Boulder, CO (US); Ivan Faul, Boulder, CO (US); Ronald M. Pasquini, Niwot, CO (US); Daniel J. Harrison, Nederland, CO (US)

(73) Assignee: Image Guided Technologies, Inc., Boulder, CO (US)

(21) Appl. No.: 09/640,794

(22) Filed: Aug. 18, 2000

Related U.S. Patent Documents

Reissue of:
(64) Patent No.: 5,907,395
Issued: May 25, 1999
Appl. No.: 08/870,296
Filed: Jun. 6, 1997

(51) Int. Cl.
*G01B 11/26* (2006.01)
*A61B 19/00* (2006.01)

(52) U.S. Cl. ..... 356/139.03; 356/141.5; 356/614; 600/476; 606/130

(58) Field of Classification Search ..... 356/139.03, 356/141.5, 375; 600/476; 606/130
See application file for complete search history.

(56) References Cited

U.S. PATENT DOCUMENTS 4,099,879 A * 7/1978 Britz ..... 356/141.5
4,193,689 A * 3/1980 Reymond et al. ..... 356/139.03
4,209,254 A * 6/1980 Reymond et al. ..... 356/139.03
4,836,788 A * 6/1989 Kato et al. ..... 438/75
4,896,673 A * 1/1990 Rose et al. ..... 600/439
5,047,776 A * 9/1991 Baller ..... 342/52
5,198,877 A * 3/1993 Schulz ..... 356/614
5,279,309 A * 1/1994 Taylor et al. ..... 600/595
5,622,170 A * 4/1997 Schulz ..... 600/424

* cited by examiner

*Primary Examiner*—Mark Hellner
(74) *Attorney, Agent, or Firm*—McCracken & Frank LLP

(57) ABSTRACT

Improved point source electromagnetic radiation emitters including a dispersing element that radiates electromagnetic radiation over a vary wide conical angle of approaching about 180°. This light dispersing element can be in any one or more of several illustrated forms such as a light diffusing spherical or hemispherical element, a planar diffusing plate, a tapered light guide, a piano-concave lens, a convex mirror, a light pipe with a large numerical aperture, or the like. The emitter of this invention may be fixed to an object and tracked in a 3-dimensional volume by a system using electro-optical position sensors in order to determine the spatial location of the emitters and therefore to determine, by geometry, the position or orientation of the object. The electromagnetic radiation generator is preferably disposed remote from the emitter and is electrically and magnetically isolated from the emitter. A common optical fiber provides transmission of the radiation from the generator to the emitter. The emitted radiation more nearly resembles point source of radiation and therefore enables more accurate determination of the location of the radiating element, and thereby more accurate determination of the position and orientation of the object on which the emitters reside. The preferred electromagnetic radiation generator is an LED, most preferably a laser diode.

71 Claims, 5 Drawing Sheets

OPTICAL FIBER PROBE FOR POSITION MEASUREMENT

Matter enclosed in heavy brackets [ ] appears in the original patent but forms no part of this reissue specification; matter printed in italics indicates the additions made by reissue.

This invention relates to improved emitters of electromagnetic rays. It more particularly refers to such emitters that are more nearly perfect point sources of electromagnetic rays than have been available in the prior art. It also refers to a novel method of determining the location of points in three dimensional space using such nearly perfect point sources of electromagnetic radiation.

BACKGROUND OF THE INVENTION

The electromagnetic rays to which this invention refers are often, but not necessarily, in the viable spectrum. The substantially point source emitters of this invention are suited to be disposed on a supporting object, of known size and shape, whose position and orientation are being determined in a three dimensional coordinate system from a determination of the locations of these emitters in the same coordinate system. They may also be disposed on one or more stationary and/or moving objects, of known size and shape, whose position(s) and orientation(s) and being tracked as it moves in space within a three dimensional coordinate system. In this use as a position and orientation determinant, the emitter is seen by a plurality of electromagnetic ray receptors, which are generally referred to herein as cameras.

The straight ray lines between a plurality of either the emitter(s), or the camera(s), or both, can be compared to straight reference lines to thus form a plurality of angles from which geometric information is obtained. This geometric information can, in turn, be used to determine the precise location(s) of the emitter(s) in space, and from these emitter locations, if the shape and size of the object are known, the position and orientation of the object on which the emitter(s) reside can be determined geometrically. Since the location of the emitter(s) can be tracked substantially continuously, or at least very frequently, movements of the object on which they are disposed can be tracked. The more frequently the locations of the emitters are determined, the more precise is the movement tracking ability of the system. Further, the smaller and less variant the emitter source of the electromagnetic rays, the more accurately can its location be determined. That is, the closer the emitter assembles a point source, which is in the same apparent location [is] *in* space regardless of the angle from which it is viewed by the camera(s), the more accurate can its locations be determined in a three dimensional coordinate system. It follows that the more accurate is the determination of the location of the point sources, the more accurate is the determination of the position(s) and orientation(s) of the object(s) supporting the emitters.

Systems for tracking or determining the position and orientation of objects in space by means of measuring the angles intersected by beams of emitted electromagnetic radiation, either between two such beams, or between one such beam and a reference beam or line, are known. Reference is made to U.S. patent application Ser. No. 08/317,805, now U.S. Pat. No. 5,622,170, the entirety of which is incorporated herein by reference, which discloses a system for determining the spatial position and orientation of the object, by means of determining the location of emitters of electromagnetic rays which are disposed on its surface, using electro-optical sensors. In order to improve their accuracy, there is a desire for these emitters to more closely approximate or resemble a point source of emitted radiation.

As referred to herein, a point source emitter(s) are tiny, but finite dimensioned, radiating (sometimes luminous) bodies. These emitters, may themselves be the object that is being tracked. Alternatively, they may be of a size which is comparable to the size of the object on which they are disposed. However, in most applications, the emitters of this invention are usually (of) much smaller than the size of the object on which they are disposed. Commonly, these emitters are many orders of magnitude smaller than the volume of the three dimensional space in which the object is being located or tracked. Thus, in relation to the volume of space in which the tracked object may be moving, the emitter can be considered to have insignificant dimensions. Because of its small size, and without considering the particular emitter shapes described by the practice of this invention, the shape of the emitter can also be considered to be of no practical consequence. However, the emitters are preferably symmetrical and, ideally, should be spherical, or at least approaching spherical.

Various electro-optical methods have been described in the prior art to determine the location of a point-like emitter of electromagnetic energy within a three-dimensional (3-d) volume relative to some reference coordinate system. If there are multiple such emitters mounted at known locations on a substantially rigid object, determining the location coordinates for each emitter in the reference system can enable the determination of the position and orientation of the object, and therefore, if the size and shape of the object are known, the location of any particular point on the object can be determined in relation to the reference system.

One such method employs multiple angle-measuring optical sensors, wherein multiple sensors are used to determine the location of one or more emitters. The locations of a plurality of electromagnetic energy emitters may be determined with respect to one, two or three angular dimensions. With the plurality of electromagnetic energy sensors (cameras) appropriately situated in known or determinable locations within a coordinate, the 3-dimensional coordinates of the emitter(s) can be determined relative to the coordinates system with a significant degree of accuracy.

For example, each of two or more spaced-apart standard video cameras, situated at one or more known spatial positions, respectively, within a three dimensional space defined by some reference coordinate system, can observe the elevation and azimuth angles of the image of an infrared light emitting diode (LED) with respect to the local optical and mechanical axes, of each camera. An appropriately programmed electronic computer with appropriate software (both of which are per se conventional as regards the instant invention) can convert those angles and the position coordinates of the cameras into 3-dimensional rectangular coordinates of the location of each LED emitter with respect to each camera and therefore with respect to the reference coordinate system as a whole. Alternatively, a plurality of two or three or more, optical angular position sensors, for example, situated appropriately with respect to each other and at known, or determinable, positions in the coordinate system, can measure the location of each LED emitter. This operation of determining the three dimensional coordinates of a point radiating source is referred to as digitizing that point in space.

A number of such electromagnetic sensors have been described in published literature and have been used in spaced apart pairs or triples to determine the location of an electromagnetic radiation emitter in 3-dimensional space. A commercially available example is the FlashPoint 5000 system, manufactured by Image Guided Technologies of Boulder, Colo. That and other examples of systems using linear (one-dimensional) detectors are described in the following references to the state of the prior art:

FlashPoint 5000 Users Manual; Image Guided Technologies, Inc., Boulder, Colo., 1996.

H. Fuchs, J. Duran, B. Johnson, and Zvi. M. Kedem; "Acquisition and Modeling of Human Body Form Data", Proc. SPIE, v. 166, 1978, p 94–102.

Jean-Claude Reymond, Jean-Luc Hidalgo; A System for monitoring the movements of one or more point sources of luminous radiation, U.S. Pat. No. 4,209,254, Jun. 24, 1980.

Y. Yamashita, N. Suzuki, M. Oshima; "Three-Dimensional Stereometric Measurement System Using Optical Scanners, Cylindrical Lenses, and Line Sensors", Proc. SPIE, v. 361, 1983, p. 67–73.

F. Mesqui, F. Kaeser, and P. Fischer; "real-time, non-invasive recording and 3-d display of the functional movements of an arbitrary mandible point", SPIE Biostereometrics 602 (1985) p 77–84.

Sharon S. Welch, Kevin J. Shelton, and James I. Clemmons; A Optical position measurement for a large gap magnetic suspension system, Proc. of the 37th International Instrumentation Symposium, San Diego, May 5–9, 1991, p. 163–182.

Waldean A. Schultz; A Method and apparatus for three-dimensional non-contact shape sensing, U.S. Pat. No. 5,198,877, issued Mar. 30, 1993.

Farhad Daghighian; A Optical position sensing with duolateral photoeffect diodes, Sensors, 1994 November, P. 31–39. Examples of systems using two-dimensional detectors are found in the following references, which reflect the state of the prior art:

U.S. Pat. No. 4,896,673 by Rose et al.

U.S. Pat. No. 4,836,788 by Baumrind et al.

Provided there is a way to distinguish between the emissions of multiple electromagnetic energy emitters (for example LED's) that are mounted on a substantially rigid object, of known size and shape, the position and orientation of the object can be geometrically derived from the determined location of the several emitters. To at least a limited extent, even the shape of an unknown object can be determined if a sufficient number of LED emitters are attached to each of its [surface] *surfaces* (see for example the '788 patent cited above). The more complicated the shape of the object, the more emitters are required to define its shape. Each emitter may be distinguished by a unique emission wavelength, by its relative location in some unambiguous geometrical pattern of emitters, or by its ordinal position in a serial emitting sequence. It is possible that other means of distinguishing between several emitters are known or will be discovered in time.

To date, in the field of tracking objects moving in space, the electromagnetic energy emitters, whose locations are to be determined, have usually been visible or infrared, light emitting diodes (LED's). Other wavelengths of electromagnetic radiation, in addition to the visible spectrum, are also well suited to use in this environment. The specific wavelength of the emitted radiation is not a limitation on the practice or scope of this invention.

Unfortunately, a conventional LED, which radiates in any given, predetermined wavelength, has several drawbacks to its use as a point source electromagnetic energy emitter. At the present time, electromagnetic energy emitting, semiconductor chips (LED's) are conventionally disposed in a protective, substantially transparent epoxy envelope. Protecting the semiconductor chip, and its electrical connections, are extremely important. However, [One] *one* drawback of this necessary epoxy envelope is that it refracts the light rays that are being emitted by the chip, which shifts the apparent optical location of the chip. Viewing the chip through the epoxy envelope from different angles generally shifts its apparent location because of this diffraction.

A second drawback is that the LED semiconductor chip, which may be as large as 1 millimeter square and is usually mounted on a partially reflecting surface, does not radiate uniformly, even without the protective epoxy coating. This can cause an apparent shift in the location of the centroid of illumination as the cameras' view of the chip is rotated about the geometrical centroid of the chip. Furthermore, the chip typically has attached to its top, an electrical contact wire or metallic strip, which partially eclipses (or reflects) the light from part of the chip and introduces asymmetry into the radiation pattern. These effects limit the accuracy and repeatability of precisely locating the chip optically, particularly if the goal is to determine a coordinate that has a smaller margin of error than the size of the chip.

A third drawback occurs when the LED's are sequentially flashed as a way to unambiguously identify individual LED's. The flashing may generate electromagnetic interference unless the waveform of the current flow through each LED is carefully controlled Even in that case, the wires to the LED's tend to act as antennae, transmitting out other electronic noise from the control box, which in practice generates high frequency control signals which are often picked up by the electromagnetic sensor assembly.

A fourth drawback exists when the LED's are used within a surgical (medical environment. The electrical current driving each LED must be very well isolated from ground, from the patient, and from all other electrical currents, including the electrical currents driving other LED's and/or other functions. Failure to completely isolate these electric currents can cause serious difficulties and even injury.

A fifth drawback exists when the LED's are used within a medical nuclear magnetic resonance imager (MRI). The metal electrical leads, the currents flowing through them, and the metallic case or heat sink (if used) deforms the MRI=s magnetic fields and thereby can warp the image of the patient.

A sixth problem occurs in designing a practical probe, a surgical instrument, or other such object, with LED's mounted on it. To reduce maintenance costs, the design should allow a burned-out LED to be replaced (and preferably to be replaced easily). Otherwise every time an LED becomes dysfunctional, the whole object/probe must be discarded and replaced. Generally, making the LED replaceable means using some kind of socket to house the LED's, which takes up additional space on the object and increases the difficulty of maintaining accurate placement of the energy emitting chip. That is, there must be a means to insure that a replacement LED chip is positioned at exactly the same effective location as the original and that all other relevant characteristics remain unchanged. If this is not accomplished, the system must be recalibrated every time an LED is replaced.

An LED as a generator of light is not a problem. In fact, an LED can be flashed much faster than an incandescent source. An LED is nearly monochromatic, allowing the position measurement sensors to use a narrow-band filter to cut out most interfering background illumination LED's are inexpensive and have a long life. A laser diode, which is a very special kind of LED, is especially good for coupling light into an optical fiber. These characteristics, and the present lack of a suitable alternative light source, suggest that LED's, or the special case laser diodes, can be expected to continue to play a role in the determination of the position and orientation of objects in space. Therefore, solutions to the above problems must be determined.

Optical fibers, or bundles of optical fibers, are a good way to transport light from a source to a destination. However, they possess a major drawback to their use as light source, in the types of system that are used for determining the locations of electromagnetic emitters, such as those described above. The drawback is that when the optical fiber end is considered to be the light source, the cone of light emitted from the end of a fiber (or fiber bundle) has an inconveniently narrow apex, or conical, angle. For the purposes of tracking an object which may have an arbitrary orientation, the light emitters on the object should ideally radiate uniformly over at least a substantial portion of a [fall] *full* hemisphere, preferably at least the entire full hemisphere, and ideally, approaching a substantial whole of a sphere.

OBJECTS AND SUMMARY OF THE INVENTION

Therefore, it is an important object of this invention to provide a new practical and effective way to produce substantially point source emissions of electromagnetic ray energy from locations on objects to be tracked in three dimensional space by an electro-optical location determination system.

Another objective of the present invention is to improve how relatively tiny point source emitters of electromagnetic ray energy are implemented, particularly where the locations of the emitters are to be tracked in three-dimensional space using an electro-optical position determining system.

A further object of this invention is to provide means for ameliorating each of the drawbacks listed above.

Other and additional objects of this invention will become apparent from a consideration of this entire specification including the drawing hereof.

This invention will be described through the example of the use of multiple emitters of light attached to a probe, which is to be used for pointing purposes in relation to a given three dimensional space (a 3-d volume). It is to be understood that this descriptive reference is only for illustration purposes. The object having electromagnetic ray emitters disposed thereon could be any objective, or a plurality of objects, whose position(s) and orientations are to be tracked within a 3-d volume with respect to a coordinate system. Examples of such objects are a robot arm, an observer's head in a virtual reality display system, a 3-d computer, a mouse, a surgical instrument, a patient on which the instrument is being used, or the like, or even combinations of such objects.

Each emitter of the present invention is suitably illustrated by a laser diode or LED, but other light sources can be used. Suitably, a lens couples the electromagnetic rays emerging from the light source into one end of an optical fiber bundle, and an optical element (the substantial point source electromagnetic emitter of this invention) at the other end of the fiber or fiber bundle suitably disperses the light into a very wide and substantially uniform emission pattern. Specifically, it is this dispersing optical element on the end of an optical fiber, and its use in the context of 3-d object tracking, to which this invention refers.

BRIEF DESCRIPTION OF THE DRAWINGS

The accompanying figures, which form a part of the specification, illustrate a preferred embodiment of the present invention and some variations thereof. Together with the textual description, these figures serve to explain the principles of the invention. A specific reference number in the figures consistently refers to the same component of the invention throughout all the figures and in the textual description.

The components of the conventional digitizing and mensuration system that are used in one aspect of the invention as shown in FIG. 1 include: an object 12 to be tracked in a 3-d volume relative to a reference coordinate system 10. The particular object to be digitized in a 3-d volume relative to a reference coordination system. One example of this object that is depicted in the figures is a stylus or probe with a tip 14 which may be used for pointing purposes. In FIG. 1, emitters 18 are shown in their conventional configuration. In FIG. 2, two laser diodes 20 are shown as the generators of light (the light sources). This invention contemplates any number of light sources, but only two light sources are shown in order to keep the figures uncomplicated. Lenses 22 couple the light from the corresponding sources 20 into one end of the optical fiber (or bundles of fibers) 24 which serve to transmit the light to the emitters 26. Each generic optical emitter element 26, disposed at the other end of the fiber, or fiber bundle, disperses the light into a very wide radiation pattern 28. Optical elements 26a (specific and illustrative forms of the generic optical element 26 that have been shown in FIG. 2) shown in FIGS. 3a and 3b are, respectively, a diffusing sphere and a diffusing plate. Another optical element 26b, shown in FIG. 4, is a tapered light pipe or image guide of special configuration sufficient to emit light dispersed in a substantially hemispherical pattern. A further optical element 26c, shown in FIG. 5, is a special concave lens.

Figure 1:
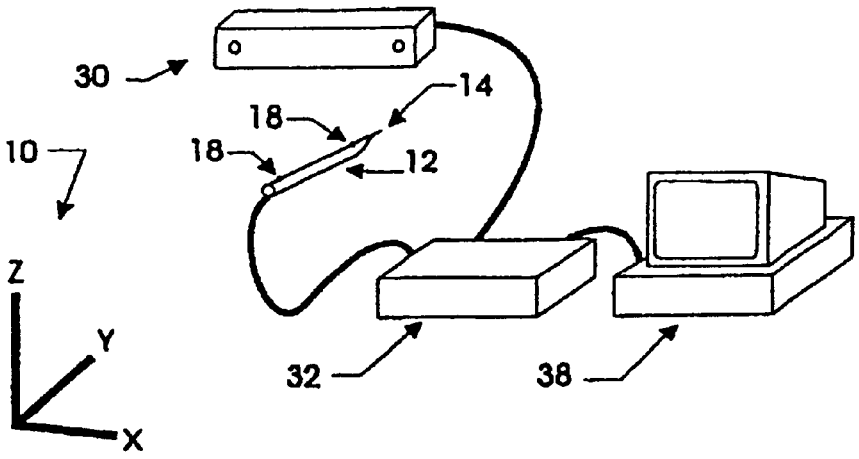
FIG. 1 is a schematic view of an otherwise conventional system that can adopt the use of the instant invention.

Exemplary rays of light 28 are radiated outward by each of the optical elements, a few of which are [Aseen≅] *seen* by the sensor assembly 30 (see FIG. 1). A support electronics system 32 powers and controls the sensor assembly 30 and the light sources. The support electronics 32 also processes the input from the sensor assembly 30. An otherwise conventional electronic computer 38 receives the input of the data from the support electronics 32. From these data, the computer 38 calculates the XYZ coordinates of the location of each optical element, 18 or 26, etc, which appears as a substantial point source emitter of light. From the thus determined coordinates of each emitter, and the known geometry of the probe, the computer 32 also computes the position and orientation of the probe and therefore determines the location of the probe tip. It also determines a unit 3-d vector describing the longitudinal direction of the probe (which is one aspect of the orientation of the probe). If more than two non-collinear electromagnetic energy ray emitters are disposed on the probe, a transverse 3-d vector can also be computed to describe its rotational orientation (or its A roll angles). The various figures are numbered throughout as follows:

| | |
|---|---|
| 10 | reference 3-d coordinate system (rectangular) |
| 12 | object to be tracked (such as a probe, as shown) |
| 14 | tip of probe |
| 18 | conventional optical emitters |
| 20a, . . . | laser diodes |
| 22a, . . . | coupling lenses |
| 24a, . . . | optical fibers or bundles of optical fibers |
| 26 | optical element (general) |
| 26a | optical element: diffusing sphere or plate |
| 26b | optical element: tapered light pipe |
| 26c | optical element: concave lens |
| 30 | sensor assembly of position measurement system |
| 32 | emitter and sensor support electronics |

The invention will be described below with reference to the figures and the numbered individual components therein. In the description below, the specific construction, the number, arrangement of the components are all intended for simplicity of explanation. Other construction, number and arrangements of the same functional components constitute, encompassed alternative embodiments of the instant described method and apparatus.

DETAILED DESCRIPTION OF THE INVENTION

Figure 2:
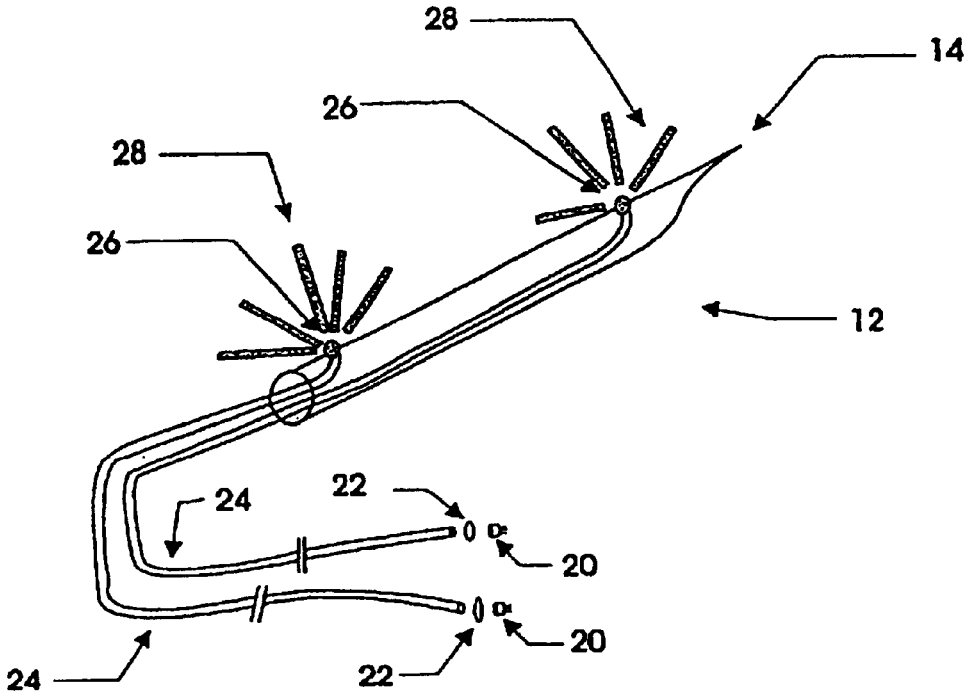
FIG. 2 is a perspective view of a probe, light source and optical fiber light guides.

In reference to FIGS. 1 and 2, note should be taken that the present invention can use substantially the same supporting equipment as was used in prior art systems. This equipment consists of an electro-optical sensor assembly 30 (e.g. the camera array), an electronic control box 32, and an electronic computer 38. The only difference between the support components used in this invention and those used in prior art systems is that in the prior art the control box 32 usually generated electrical pulses to fire the LED's 18, that are shown in FIG. 1 to have been previously disposed on the probe 12 (or another such object to be tracked). In the present invention the same electric pulses fire the laser diodes 20 of FIG. 2, which are, at least in a preferred mode, preferably disposed remote from the object 12 being tracked. The laser diodes 20 are preferably located in the control box 32 itself in order to limit their emission of spurious electromagnetic radiation. Alternatively, the laser diodes 20 can be housed in a separate box or even in the handle of the probe 12 itself. Although there may be some disadvantages to situating the light sources within the probe body because stray radiation might interfere with other surrounding operations as aforesaid, there is a distinct economic advantage to situating the ultimate light sources within the probe handle. The advantage of this option is that a probe of the prior art could be upgraded to a probe of the present invention without requiring any change to the supporting equipment. This may be an advantage in connection with some existing systems, particularly where cost of upgrading is a factor. In either case, the operation of the system of this aspect of this invention is substantially the same regardless of where the ultimate light source is located. In a preferred embodiment, the ultimate light source is remote from the emitter, but it does not absolutely have to be so. In this regard, the instant invention enables owners of prior systems to upgrade them to the system of this invention without substantial remodeling costs.

Just as in the prior art, the laser diodes 20 can be sequentially activated (flashed) and there light transmitted to their respective emitters according to this invention, and thereby these emitters will flash sequentially and they can then be located individually. Alternatively, each of the laser diodes 20 can be controlled to operate continuously, rather than sequentially. In this aspect of this invention, each laser diode will be set to generate different wavelengths of light rays 28, respectively, in order to uniquely identify each of the point source emitters of light 26. Alternatively still, the optical elements 26 can be disposed in such a geometric pattern that the optical elements are unambiguously identified by their location (such as at the vertices of an irregular polygon or polyhedron).

In any case, the sensor assembly will sense these emissions and will return raw data of the location of each emitter through the control box 32 to computer 38 which is running a software program to compute XYZ coordinate relative to the coordinate system 10 form the raw sensor data. In practice the raw data from the sensor assembly 30 could be analog data which the control box 32 could convert to digital data. The final 3-d coordinate computation would been done by the computer 38 which could be a standard personal computer or workstation. Of course, this invention is not limited to the specific computer that is chosen for implementation of the mensuration aspects hereof.

The sensor assembly 30, the supporting control electronics 32, and the calculations in the computer 38 are not substantially different from the prior art. Therefore, no further details about them will be discussed. They could be off-the-shelf, commercially available systems, and therefore they are disclosed herein only by reference to the above mentioned technical papers and patents.

Four alternative embodiments of the optical emitter elements will be presented. Each operates slightly differently, but the effect is the same: light from a suitable source, such as a laser diode, is transmitted through the optical fiber to a suitable emitter, and then radiates in a much wider cone than it would have from the fiber alone without the intervention of the optical emitter elements. Furthermore, the sensor sees the effective point from which the light appears to come is tiny, and its centroid does not vary with the orientation angle of the optical emitter element with respect to the sensor assembly. If the light sources, for example laser diodes, or LED's, are housed in the control box 32 and it is well shielded against spurious electromagnetic radiation, no, or at least only a very small amount of spurious electromagnetic radiation will escape, and only the intended light will be transmitted inside the optical fiber(s). The probe can be designed to be completely neutral electrically and magnetically. Therefore, the probe can be designed to be wholly non-metallic. Lastly, in the configuration of this invention, the optical fibers and optical emitter elements do not burn out and can be made to be as small as, or even smaller than, LED light sources. In addition, these light emitter elements used in this invention operate directly and without sockets. On the other hand, the hand, the laser diodes, which are subject to burning out and need to be replaced, can be situated where they can be readily replaced as necessary (such as inside the control box 32. In a less preferred embodiment of this invention, they can be disposed in the handle of the probe itself). The location of the actual light which is the origin of the radiation being emitted by the practice of this invention can be made by the system designer without affecting the practice of this invention. It is to be understood that in a preferred embodiment of this invention, the electrically driven light source is spatially removed from the probe itself.

The optical fibers 24 themselves can be any diameter, such as for example 400 microns. That is, they might be finer and lighter than the wire pairs that were previously used to power the light sources. Yet, they can be large enough to simplify the problem of efficiently coupling in the light from the laser diodes 20 to the optical fiber or fiber bundle. Because the distances traversed by these optical fibers 24 are so short, and the information they carry is so simple, the fibers 24 can sustain higher internal losses than long-distance communication fibers. For example, they could be inexpensive plastic, such as polymethyl methacrylate, instead of the more expensive and lower loss silica.

Figure 3A:
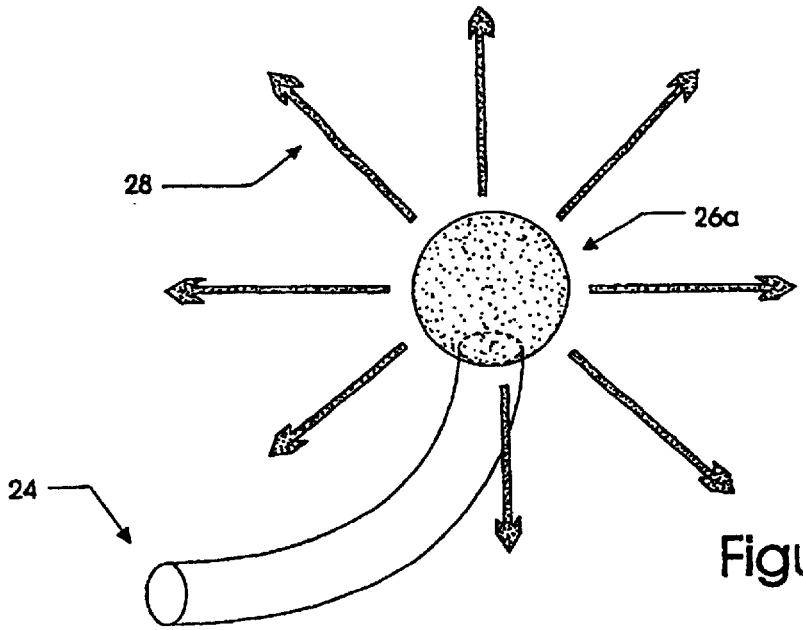
FIG. 3a is a plan view of one aspect of a point source emitter according to this invention.

A first embodiment of the critical optical element 26 of this invention is shown in FIG. 3a. In this case the light is uniformly and widely dispersed by means of a tiny diffusing sphere 26a which is optically coupled to the end of the optical fiber. This is the preferred embodiment of this invention because it can very uniformly disperse light omni-directionally (in substantially all directions). Such diffusing spheres are, for example, manufactured by Rare Earth Medical, Inc. (West Yarmouth, Mass.) for use in laser oblation surgery (but not for geometrical localization purposes). Such diffusing spheres are transparent epoxy balls with minute particles of reflective powder suspended inside. The combination of light reflecting off the particles and refracting around them scatters the light in all directions quite uniformly. The only drawback to this embodiment occurs when a sphere is partially eclipsed by the handle of the probe (or other such object). In this [Asunset≅] *sunset* situation, the centroid of the visible portion of the square will shift away from the geometrical center of the sphere.

Figure 3B:
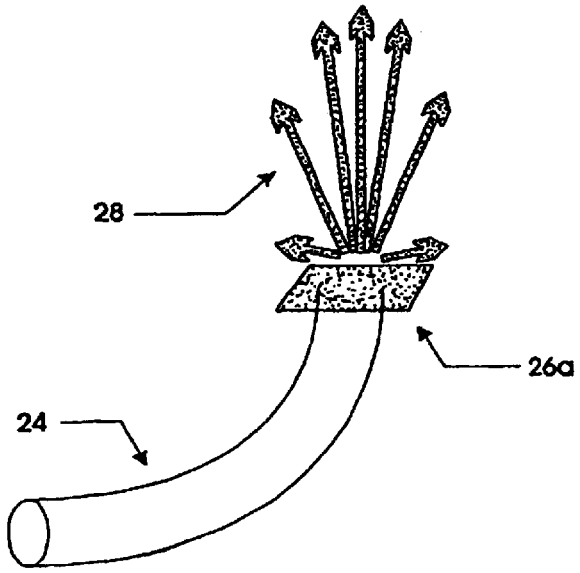
FIG. 3b is a perspective view of one embodiment of this invention.

The sunset situation can be eliminated by using a planar diffuser, such as the one shown in the configuration depicted in FIG. 3b rather than a sphere as shown in FIG. 3a, and insuring that its plane is tangent to the curve of the probe handle. If the planar diffuser 26a is viewed from a normal direction (that is, head-on), the narrow cone of light emitted from the optical fiber 24 creates a bright luminous circular disk on the diffuser 26a. As this disk is viewed from larger angles from the normal, the disk appears as an ellipse, but the centroid remains in the middle. The light intensity distribution from this configuration is Lambertian; that is, most of the light is radiated *in* a direction that is normal to the plate, and less is dispensed at larger angles with respect to the normal direction. Mathematically, the intensity is proportional to the cosine of the viewing angle, as measured with respect to the normal direction. For example, the intensity falls to zero as the viewing angle approaches 90 degrees from normal.

Figure 4:
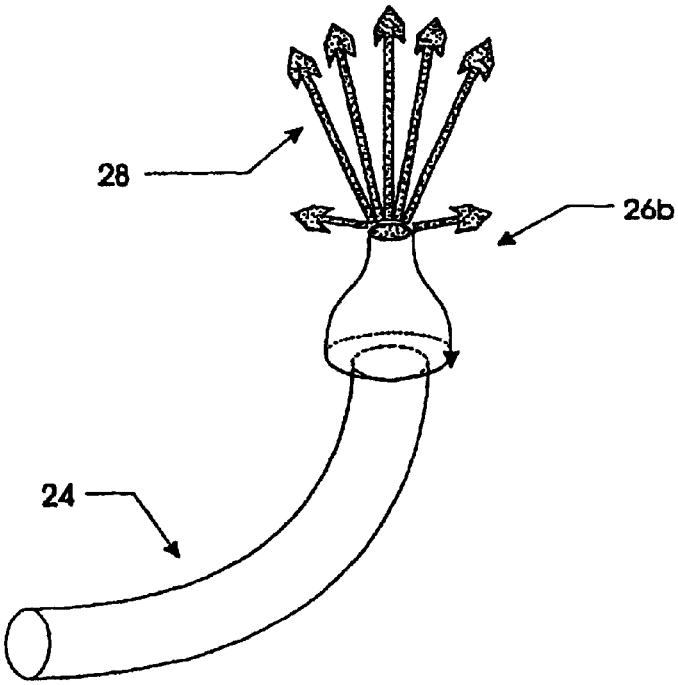
FIGS. 4, 5, 6, 7 and 8 are perspective views of other embodiments of this invention.

A second embodiment of the optical element 26 of this invention is shown in FIG. 4. In this case the light is widely dispersed by means of a special optical fiber bundle 26b called an image guide or a light pipe. It is preferably tapered to concentrate the light into a smaller spot and it has a high numerical index to widen the emission angle of the cone of radiation. Such fiber bundles are available from Collimated Holes, Inc., (Campbell, Calif.).

In any embodiment of this invention, the optical fiber bundles may be randomly organized and need not preserve image geometry because they are only being used as light transmitters. If the fibers of the light pipe have a high index of refraction (a numerical aperture value near 1.0), the light will be radiated through out substantially, a full hemispherical pattern. Even though the intensity of light diminishes with the cosine of the angle of the direction of radiation (measured relative to the optical axis of the fibers, far more light is radiated in directions which are substantially parallel to the axis of the fibers and much less at steeper angles) Even so, there is sufficient radiated light to be "seen" by the camera array. This is shown in FIG. 4, as a higher concentration of rays 28 in the forward direction (that is substantially parallel to the axis of the fiber than in a direction normal to the fiber axis.

Note that in the embodiment shown in this figure, the whole optical fiber 24 and the light pipe 26b could be one and the same element if they were properly designed. That is, the optical fiber 24 may simply be a long flexible light guide with a large (wide) numerical aperture at its end. Conventional optical fibers have not been found to produce satisfactory large conical emission angles, without first being modified. [Therefore, this aspect of this large conical emission angles, without first being modified.] Therefore, this aspect of this invention has been developed specifically to overcome this deficiency.

Figure 8:
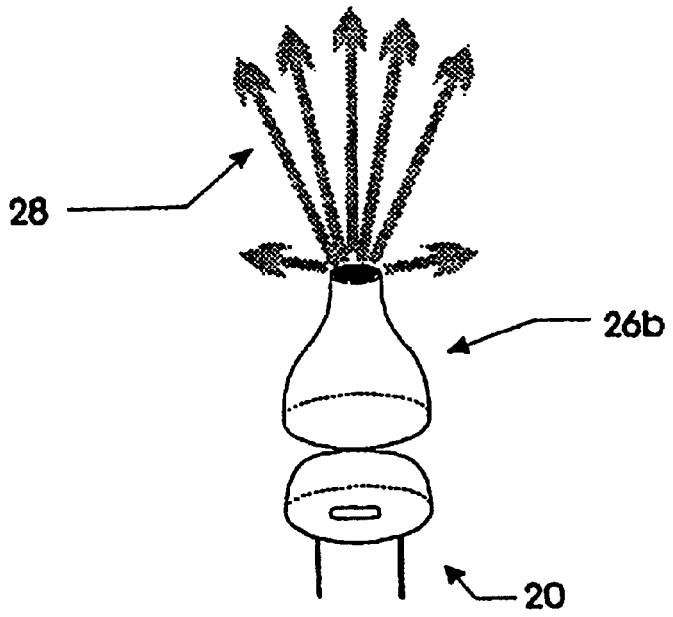

Note should be taken that, in the embodiment shown in this FIG. 4, the optical fiber 24 and the coupling lens 22 could be omitted and the light source 20 could be placed directly within the probe directly behind the optical element 26. While this does not avoid creating electronic and magnetic interference (because an electrical cable to the probe would then be required), it still overcomes some of the disadvantages listed in the section of this specification captioned. Background of the Invention. However, even though this alternative is considered to be within the scope of this invention, this is not a preferred embodiment of this invention. In this regard, note should be taken of the configuration shown in FIG. 8.

Figure 5:
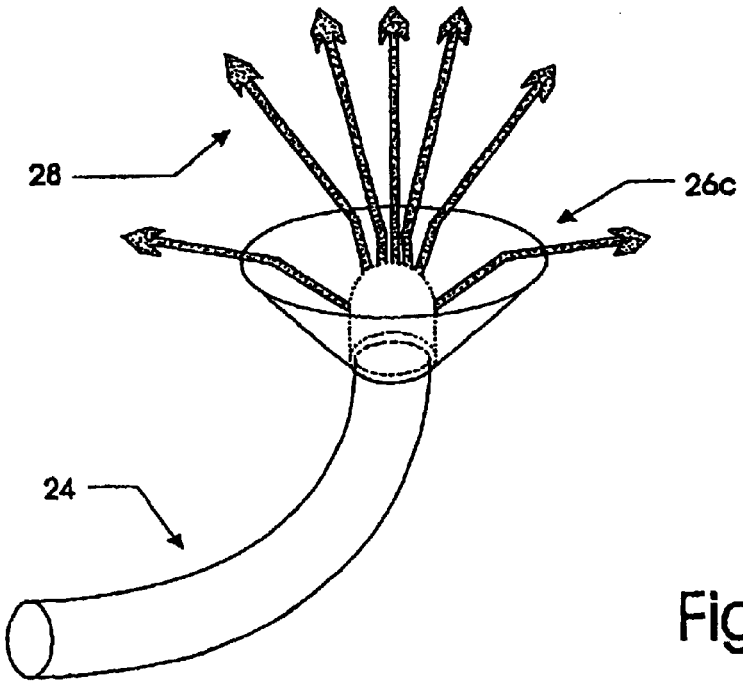
Figure 6:
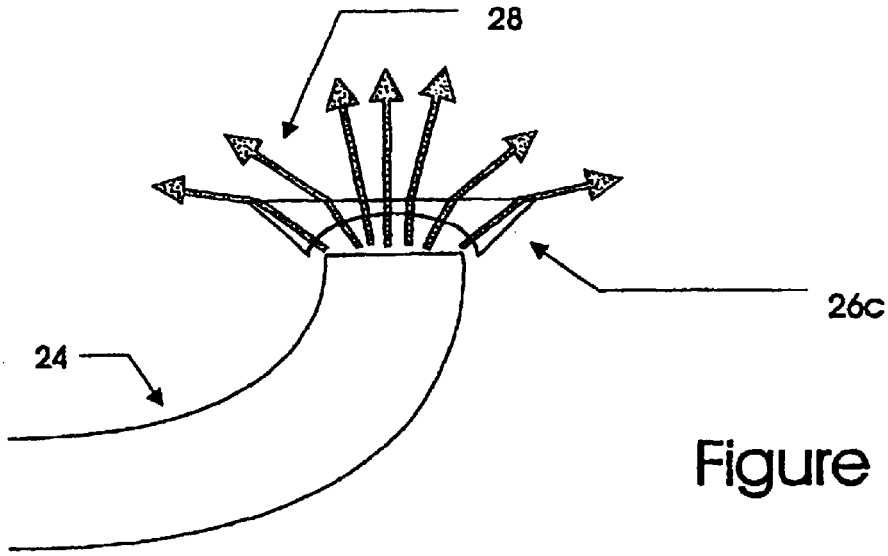

A third embodiment of the optical element 26 is shown in FIGS. 5 and 6. FIG. 5 is an oblique view and FIG. 6 is a cross-section view showing in better detail the action of the lens of this embodiment on the rays of light. In this case, the light is widely dispersed over a substantially complete hemisphere by means of a tiny concave lens 26c. The lens is designed to produce a tiny virtual image of the end of the optical fiber which is visible even at very extreme angles. That is, the light is not only radiated in the "forward and near forward directions", that is substantially parallel to the axis of the transmitting optical fiber, but it is not radiated in directions which approach being parallel to the planar surface of the lens, that is substantially transverse to the axis of the optical fiber or fiber bundle. Note that if the end(s) of the transmitting optical fiber is rounded, or a convex lens or optically transparent ball is placed over the end of the fiber, the emitted light will diverge somewhat, but the angle of the cone of emitted light does not exceed approximately 90 degrees, which is still too narrow to be practical without further modification by the further use of a lens of this embodiment. For this reason, it is most preferred to use a concave lens. In this regard, a rounded end of the optical fiber coupled with a concave lens will be quite effective.

Figure 7:
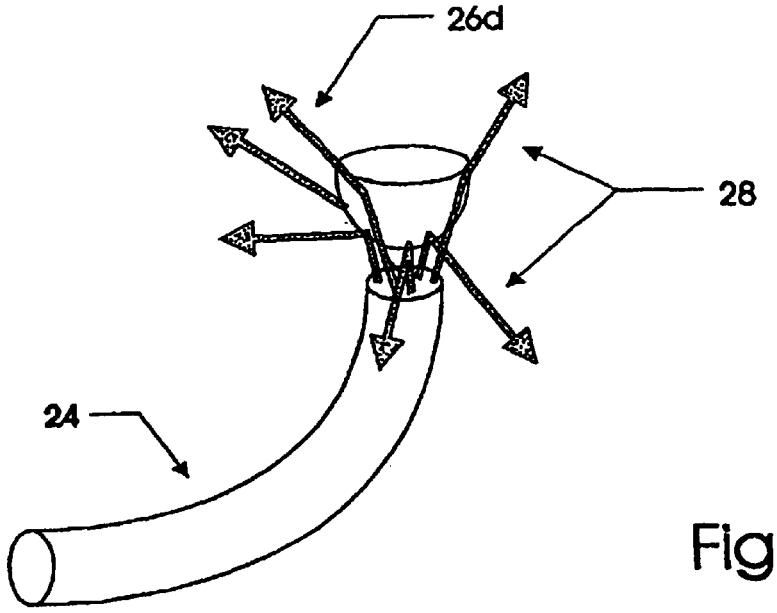

A fourth embodiment of the optical element 26 of this invention is shown in FIG. 7. In this embodiment, the light coming out of the transmitting optical fibers is reflected off of a tiny curved (hyperbolic) mirror 26d. This is the reflective optical counterpart to the refractive element 26c shown in other figures. The advantage of this arrangement is that the light can be spread over a wide annular ring of angles. The drawback to this arrangement is that the optical fiber or the mirror itself eclipses the reflected light at angles near the optical axis (both forward and backward).

The above description has presented four specific embodiments of the operationally substantially at least hemispherical optical radiating elements of this invention. Each of these embodiments is illustrative of the instant invented means of making optical fibers practical for use in an electro-optical system for tracking an object, such as a probe or pointer, with two or more point source light emitters. The optical elements facilitate increased accuracy, nearly perfect electrical and magnetic isolation, and no generation of spurious radiation. The passive optical fibers on the object itself potentially reduce the cost enough that disposable surgical probes would be economically feasible. Further, the optical fibers are more robust than LED's and are therefore more suitable for autoclaving in medical environments. Lastly, the optical light source can be a laser (diode or gas) which has the potential for generating more light than the simple LED used in the prior art.

While this invention has been described above with reference to several preferred embodiments, a person of ordinary skill in the art should be able to readily visualize alternative embodiments which do not materially depart from the scope of this invention. Therefore, the scope and content of this invention are not limited by the foregoing description. Rather, the scope and content are to be defined by the following claims.

What is claimed is:

1. An apparatus for determining the location of at least one point in three dimensional space relative to a three dimensional coordinate system defining said space comprising:

at least one emitter of electromagnetic radiation, comprising a radiation dispersing element which emits said radiation in a substantially conical pattern which at least approaches a [solid angle of about 180°] *hemisphere,* wherein said radiation emission pattern has a centroid such that it at least closely approximates a point source of said radiation thereby causing said centroid of said electromagnetic radiation to be in a substantially invariant relationship to said emitter of said radiation regardless of the angle from which the centroid of the emitted radiation is viewed;

an electromagnetic radiation generator operatively associated with each of said emitters;

means for transmitting electromagnetic radiation generated by said generator to said emitter;

a plurality of electromagnetic radiation sensors, each of which is adapted to detect at least one electromagnetic ray emitted from at least one of said emitters;

a power supply for said electromagnetic radiation generator;

where there are a plurality of emitters, means to differentiate electromagnetic radiation emitted by at least two of said emitters; and means for determining the location of said emitter relative to the three dimensional coordinate system;

wherein, as a consequence of said emitters emitting electromagnetic radiation at a solid angle of at least approaching [180 °] *a hemisphere* determining the location of a said emitters with greater accuracy than would have been the accuracy determined had the electromagnetic radiation been generated without said dispersing element.

2. The apparatus as claimed in claim 1, wherein at least one of said dispersing element comprises a diffuser.

3. The apparatus as claimed in claim 2, wherein the diffuser is substantially a section of a sphere.

4. The apparatus as claimed in claim 2, wherein the diffuser is substantially flat.

5. The apparatus as claimed in claim 1, wherein at least one of said emitters comprises a light pipe image guide which is so shaped as to be capable of emitting electromagnetic radiation from an end thereof at a solid angle at least approaching [180°] *a hemisphere*.

6. The apparatus as claimed in claim 1, wherein at least one of said emitters comprises a concave lens with a negative focal length capable of emitting electromagnetic radiation at a solid angle at least approaching [180°] *a hemisphere*.

7. The apparatus as claimed in claim 1 wherein at least one of said emitters comprises a curved, convex mirror capable of emitting reflected electromagnetic radiation at a solid angle at least approaching [180°] *a hemisphere*.

8. The apparatus as claimed in claim 1 wherein said electromagnetic radiation comprises visible light.

9. The apparatus as claimed in claim 1 wherein said electromagnetic radiation comprises infra red light.

10. The apparatus as claimed in claim 1 wherein said electromagnetic radiation comprises ultra violet light.

11. The apparatus of claim 1 comprising a plurality of emitters.

12. The apparatus as claimed in claim 1 comprising a separate electromagnetic radiation generator associated with each emitter.

13. The apparatus as claimed in claim 11 wherein each of said emitters radiates at a different wavelength.

14. The apparatus as claimed in claim 1 wherein said at least one emitter is disposed on an object in said three dimensional space, and wherein said electromagnetic radiation generator is disposed proximate to said emitter.

15. The apparatus as claimed in claim 1 wherein said at least one emitter is disposed on an object in said three dimensional space, said electromagnetic radiation generator is disposed a distance from said emitter, and at least one electromagnetic radiation guide is disposed therebetween in operative relationship to both said generator and said emitter.

16. The apparatus as claimed in claim 14 wherein said electromagnetic radiation generator is disposed in or on said object sufficiently proximate to said emitter as to exclude a radiation guide therebetween.

17. The apparatus as claimed in claim 15 wherein said electromagnetic radiation generator is powered by electricity, and wherein said emitter and said objective are substantially electrically neutral.

18. The apparatus as claimed in claim 15 wherein said electromagnetic radiation generator is powered by electricity and wherein said emitter and said object are substantially magnetically neutral.

19. The apparatus is claimed in claim 15 wherein said at least one emitter is unconnected to a source of electricity.

20. An electrically neutral system for radiating electromagnetic radiation from an effective point source comprising:

an electromagnetic radiation generators;

an emitter of electromagnetic radiation comprising a radiation dispersing element which emits said electromagnetic radiation in a substantially conical pattern through a solid angle which at least approaches [180°] *a hemisphere*, wherein said radiation emission has a centroid such that it at least closely approximates a point source of said radiation thereby causing said centroid of said electromagnetic radiation to be in a substantially invariant relationship to the emitter of said radiation regardless of the angle from which the centroid of emitted radiation is viewed, and wherein said emitter is disposed a distance from said generator;

at least one optical filter disposed in operative relationship to both said generator and said emitter such that it is adapted to transmit electromagnetic radiation from said generator to said emitter; and an electric power source operatively associated with said electromagnetic radiation generator, wherein said generator is substantially electrically and magnetically isolated from said emitter.

21. The apparatus as claimed in claim 20 wherein at least one of said dispersing element comprises a diffuser.

22. The apparatus as claimed in claim 21 wherein the diffuser is substantially a section of a sphere.

23. The apparatus as claimed in claim 21 wherein the diffuser is substantially flat.

24. The apparatus as claimed in claim 20 wherein at least one of said emitters comprises a light pipe image guide which is so shaped as to be capable of emitting electromagnetic radiation from an end thereof at a solid angle at least approaching [180°] *a hemisphere*.

25. The apparatus as claimed in claim 20 wherein at least one of said emitters comprises a concave lens with a negative focal length capable of emitting electromagnetic radiation at a solid angle at least approaching [180°] *a hemisphere*.

26. The apparatus as claimed in claim 20 wherein at least one of said emitters comprises a curved, convex mirror capable of emitting reflected electromagnetic radiation at a solid angle at least approaching [180°] *a hemisphere*.

27. The apparatus as claimed in claim 20 wherein said electromagnetic radiation comprises visible light.

28. The apparatus as claimed in claim 20 wherein said electromagnetic radiation comprises infra red light.

29. The apparatus as claimed in claim 20 wherein said electromagnetic radiation comprises ultra violet light.

30. The apparatus as claimed in claim 20 comprising a plurality of emitters.

31. The apparatus as claimed in claim 20 comprising a separate electromagnetic radiation generator associated with each emitter.

32. The apparatus as claimed in claim 30 wherein each of said emitters radiates at a different wavelength.

33. The apparatus as claimed in claim 20 wherein said at least one emitter is disposed on an object in said three dimensional space, and wherein said electromagnetic radiation generator is disposed proximate to said emitter.

34. The apparatus as claimed in claim 20 wherein said at least one emitter is disposed on an object in said three dimensional space, said electromagnetic radiation generator is disposed a distance from said emitter, and at least one electromagnetic radiation guide is disposed therebetween in operative relationship to both said generator and said emitter.

35. The apparatus as claimed in claim 33 wherein said electromagnetic radiation generator is disposed in or on said object sufficiently proximate to said emitter as to exclude a radiation guide therebetween.

36. The apparatus as claimed in claim 34 wherein said electromagnetic radiation generator is powered by electricity, and wherein said emitter and said object are substantially electrically neutral.

37. The apparatus as claimed in claim 34 wherein said electromagnetic radiation generator is powered by electricity, and wherein said emitter and said object are substantially magnetically neutral.

38. The apparatus as claimed in claim 34 wherein said at least one emitter is unconnected to a source of electricity.

39. A method of accurately determining the location of a point in three dimensional space which comprises:

electrically generating electromagnetic radiation;

non-electrically transmitting said electromagnetic radiation to an emitter, comprising a radiation dispersing element, so constructed as to emit electromagnetic radiation therefrom in a conical array through a solid angle at least approaching [180°] *a hemisphere*;

non-electrically emitting said electromagnetic radiation from said dispersing element in a substantially conical pattern over a solid angle that at least approaches about [180°] *a hemisphere;* and thereby causing a centroid of said emitted electromagnetic radiation to at least closely approximate a point source of said radiation which is substantially invariant with respect to the emitter of said radiation regardless of the angle from which said emitted radiation is viewed.

40. A method as claimed in claim 39 further comprising generating said electromagnetic radiation a distance from said emitter; transporting said generated electromagnetic radiation non-electrically through at least one optical fiber from said electromagnetic generator to said emitter; and maintaining said emitter electrically and mechanically substantially neutral.

41. A method as claimed in claim 39 further including disposing at least one of said emitter on a three dimensional object; disposing an electromagnetic generator in operative association with a radiation guide in operative relationship with each of said emitters and remote from said object; and maintaining said object electrically and magnetically substantially neutral with respect to said electromagnetic generator.

42. A method of determining the position and orientation of at least one three dimensional object in a three dimensional space defined by a coordinate system which comprises:

disposing a plurality of electromagnetic emitters, comprising a dispersing element so constructed as to radiate electromagnetic radiation in a substantially conical pattern over a solid angle that at least approaches about [180°] *a hemisphere* in known spaced apart relationship to each other on a surface of said object;

providing at least one electromagnetic radiation generator spaced from said object;

providing a non-electric radiation guide operatively associated with each emitter and with said at least one generator;

generating electromagnetic radiation from each of said generators;

transmitting said radiation, non-electrically through said radiation guides to said emitters;

non-electrically radiating a substantially conical pattern of radiation from at least one of said dispersing elements;

receiving said emitted radiation by a plurality of electromagnetic radiation receivers;

determining the location of each emitter as a function of the angles between said received radiation and respective reference lines; and converting said determined locations of said emitters to a position and orientation of said object in said three dimensional space.

43. A method as claimed in claim 42 wherein said dispersing element comprises a diffuser.

44. A method as claimed in claim 42 wherein said dispersing element comprises a section of a sphere.

45. A method as claimed in claim 42 wherein said dispersing element comprises a light pipe image guide so constructed as to emit said electromagnetic radiation over a solid conical angle at least approaching [180°] *a hemisphere*.

46. A method as claimed in claim 42 wherein said diffuser comprises a substantially flat plate.

47. A method as claimed in claim 42 wherein said dispersing element comprises a concave lens with a negative focal length.

48. A method as claimed in claim 42 wherein said dispersing element comprises a convex mirror.

*49. The apparatus as claimed in claim 11 wherein at least two of said emitters rediate at a different wavelength.*

*50. An electrically neutral system for radiating electromagnetic radiation from an effective point source comprising:*

*at least one electromagnetic radiation generator;*

*at least one emitter of electromagnetic radiation comprising means for emitting radiation through a solid angle that at least approaches a hemisphere,*

*wherein said radiation emission has a centroid such that is at least closely approximates a point source of said radiation; and*

*wherein said emitter(s) is disposed a distance from said generator(s),*

*at least one optical fiber disposed in operative relationship to said generator(s) and said emitter(s) such that the fiber is adapted to transmit electromagnetic radiation from said generator(s) to said emitter(s); and*

*an electric power source operatively associated with said electromagnetic radiation generator, wherein said generator is substantially electrically and magnetically isolated from said emitter.*

*51. A method of determining the position and orientation of at least one three dimensional object in a three dimensional space, defined by a coordinate system, which comprises:*

*disposing a plurality of electromagnetic emitters, comprising a dispersing element so constructed as to radiate electromagnetic radiation over a solid angle that at least approaches about a hemisphere in known spaced apart relationship to each other on a surface of said object;*

*providing at least one electromagnetic radiation generator spaced from said object;*

*providing at least one non-electric radiation guide means operatively associated with said emitter(s) and with said at least one generator(s);*

*generating electromagnetic radiation from generator(s);*

*transmitting said radiation, non-electrically through said radiation guide(s) to said emitter(s);*

*non-electrically radiating radiation from at least one of said dispersing elements;*

*receiving said emitted radiation by a plurality of electromagnetic radiation receivers;*

*determining the location of each emitter as a function of the angles between said received radiation and respective reference lines; and*

*converting said determined locations of said emitters to a position and orientation of said object in said three dimensional space.*

*52. An apparatus for determining the location of at least one point in three dimensional space relative to a three dimensional coordinate system defining said space comprising:*

*at least one emitter of electromagnetic radiation, comprising a radiation dispersing element that is adapted to emit said radiation in a substantially conical pattern that at least approaches a solid angle at least about equal to a hemisphere;*

*an electromagnetic radiation generator operatively associated with at least one of said emitters;*

*means for transmitting electromagnetic radiation generated by said generator to said associated emitter;*

*a plurality of electromagnetic radiation sensors, each of which is adapted to detect at least one electromagnetic ray emitted from at least one of said emitters;*

*where there are a plurality of emitters, means to differentiate electromagnetic radiation emitted by at least two of said emitters; and*

*means for determining the location of said emitter(s) relative to said three dimensional coordinate system as a function of a plurality of angles intercepted between rays of said radiation and at least one reference line;*

*wherein, as a consequence of said emitters emitting electromagnetic radiation at a solid angle at least approaching a hemisphere, determining the location of said emitters with greater accuracy that would have been the accuracy determined had the electromagnetic radiation been generated without said dispersing element.*

*53. The apparatus as claimed in claim 1, wherein at least one of said emitters comprises a light pipe image guide that is so shaped as to enable emitting electromagnetic radiation from an end thereof at a solid angle at least approaching a hemisphere.*

*54. The apparatus as claimed in claim 1, wherein at least one of said emitters comprises a concave lens with a negative focal length capable of emitting electromagnetic radiation at a solid angle at least approaching a hemisphere.*

*55. The apparatus as claimed in claim 1 wherein at least one of said emitters comprises a curved, convex mirror capable of emitting reflected electromagnetic radiation at a solid angle at least approaching a hemisphere.*

*56. An electrically neutral system for radiating electromagnetic radiation from an effective point source comprising:*

*an electromagnetic radiation generator;*

*an emitter of electromagnetic radiation comprising a radiation dispersing element that emits said electromagnetic radiation in a substantially conical pattern through a solid angle that at least approaches a hemisphere, and wherein said emitter is disposed a distance from said generator;*

*at least one optical fiber disposed in operative relationship to both said generator and said emitter such that it is adapted to transmit electromagnetic radiation from said generator to said emitter; and*

*an electric power source operatively associated with said electromagnetic radiation generator, wherein said generator is substantially electrically and magnetically isolated from said emitter.*

*57. The apparatus as claimed in claim 56 wherein at least one of said emitters comprises a light pipe image guide that is so shaped as to enable emitting electromagnetic radiation from an end thereof at a solid angle at least approaching a hemisphere.*

*58. The apparatus as claimed in claim 56 wherein at least one of said emitters comprises a concave lens with a negative focal length capable of emitting electromagnetic radiation at a solid angle at least approaching a hemisphere.*

*59. The apparatus as claimed in claim 56 wherein at least one of said emitters comprises a curved, convex mirror capable of emitting reflected electromagnetic radiation at a solid angle at least approaching a hemisphere.*

*60. A method of accurately determining the location of a point in three dimensional space which comprises:*

*electrically generating electromagnetic radiation;*

*non-electrically transmitting said electromagnetic radiation to at least one emitter comprising a radiation dispersing element adapted to emit electromagnetic radiation therefrom through a solid angle at least approaching a hemisphere; and*

*non-electrically emitting said electromagnetic radiation from said dispersing element in a pattern over a solid angle that at least approaches about a hemisphere.*

*61. A method of determining the position and orientation of at least one three dimensional object in a three dimensional space defined by a three dimensional coordinate system which comprises:*

*disposing a plurality of electromagnetic emitters, comprising a dispersing element adapted to radiate electromagnetic radiation in a substantially conical pattern over a solid angle that at least approaches about a hemisphere, in known spaced apart relationship to each other on a surface of said object;*

*providing at least one electromagnetic radiation generator spaced from said emitter(s);*

*providing a non-electric radiation guide operatively associated at least one of said emitters and with said at least one generator;*

*generating electromagnetic radiation by said generator(s);*

*non-electrically transmitting electromagnetic radiation through said radiation guides to said emitter(s);*

*non-electrically radiating a pattern of radiation at least approaching a hemisphere from at least one of said dispersing elements;*

*receiving said emitted radiation by a plurality of electromagnetic radiation receivers;*

*determining the location of each emitter as a function of angles between said received radiation and respective reference lines; and*

*converting said determined locations of said emitters to a position and orientation of said object in said three dimensional space.*

*62. A method as claimed in claim 61 wherein said dispersing element comprises a light pipe image guide adapted to emit said electromagnetic radiation over a solid conical angle at least approaching a hemisphere.*

*63. An apparatus for determining the location of at least one point in three dimensional space relative to a three dimensional coordinate system defining said space comprising:*

*at least one emitter of electromagnetic radiation, comprising a radiation dispersing element that disperses electromagnetic rays emitted from said emitter in a pattern that at least approaches a solid angle at least about equal to a hemisphere and has a radiation pattern that at least closely approximates that of a point source of said radiation over said solid angle;*

*a plurality of electromagnetic radiation sensors, each of which is adapted to detect at least one electromagnetic ray emitted from at least one of said emitters, and to convert said detected ray into a signal;*

*where there are a plurality of emitters, means to differentiate at least two of said emitters; and*

*a signal processor adapted to calculate the location of said emitter(s) relative to the three dimensional coordinate system from said signal information;*

*wherein, as a consequence of said emitter(s) emitting electromagnetic radiation through said solid angle, determining the location of the centroid(s) of said emitter(s) with greater accuracy than would have been the accuracy determined had that electromagnetic radiation been generated without said dispersing element.*

*64. The apparatus as claimed in claim 63 wherein at least two of said emitters radiate at different wavelengths.*

*65. The apparatus as claimed in claim 63 wherein said dispersing element is spaced from said radiation generator and further comprising transmission means adapted to transmit said generated radiation from said generator to said dispersing element.*

*66. The apparatus as claimed in claim 65 further comprising a plurality of dispersing elements.*

*67. A method of accurately determining the location of a point in three dimensional space comprising:*

*generating electromagnetic radiation;*

*non-electrically transmitting and electromagnetic radiation to at least one emitter, comprising at least one radiation dispersing element adapted to emit electromagnetic radiation therefrom through a solid angle at least approaching about a hemisphere;*

*non-electrically emitting said electromagnetic radiation from said dispersing element at a solid angle approaching about a hemisphere;*

*receiving a plurality of electromagnetic rays, emitted by said emitter, by an electromagnetic radiation detector;*

*determining angles intercepted between said rays and at least one reference line that has a known angular relationship with said radiation detector; and*

*from said angle, calculating a location of said emitter in said three dimensional space.*

*68. An electrically neutral system for radiating electromagnetic radiation from an effective point source and remotely receiving the same, comprising:*

*at least one source of electromagnetic radiation;*

*lens means adapted to couple said electromagnetic radiation to a plurality of non-electronic radiation transmission means;*

*at least one emitter, adapted to radiate electromagnetic radiation through a solid angle that at least approaches a hemisphere, electromagnetically coupled to at least one of said transmission means and spaced apart from said source; and*

*a plurality of means adapted to receive said radiated electromagnetic radiation spaced from said emitter(s) and not electrically connected to said emitters.*

*69. A system as claimed in claim 68 comprising a plurality of said transmission means and a plurality of emitters operatively associated with said plural transmission means.*

*70. A system as claimed in claim 69 comprising a single source of said electromagnetic radiation.*

*71. A system as claimed in claim 69 wherein said receivers are adapted to convert said received electromagnetic radiation to a signal, and further comprising a computer operatively associated with said receiver(s) adapted to receive said signals and to convert said signals into location(s) of said emitter(s) in a defined three dimensional volume.*

* * * * *